(12) United States Patent
Pimentel et al.

(10) Patent No.: US 6,451,861 B1
(45) Date of Patent: Sep. 17, 2002

(54) REDUCTION OF GASTRO-INTESTINAL BACTERIAL LOAD

(76) Inventors: Julio Lionel Pimentel, 3206 Windgate Dr., Buford, GA (US) 30519-1941; Lanny U. Franklin, 5170 Chemin de Vie, Atlanta, GA (US) 30342

( * ) Notice: Subject to any disclaimer, the term of this patent is extended or adjusted under 35 U.S.C. 154(b) by 0 days.

(21) Appl. No.: 09/411,562

(22) Filed: Oct. 4, 1999

(51) Int. Cl.$^7$ .................. A61K 31/11; A61K 31/045; A61K 31/015
(52) U.S. Cl. .................. 514/703; 514/739; 514/764
(58) Field of Search .................. 514/703, 739, 514/764

(56) References Cited

PUBLICATIONS

WPIDS An 1993–115247, Lyanders et al, abstract Apr. 23, 1992.*
WPIDS AN 1998–376747, Wiersma, abstract Jun. 23, 1998.*
Bard, M, MR Albert, N Gupta, CJ Guuynn and W Stillwell, 1988. Geraniol interferes with membrane functions in strains of Candida and Saccharomyces. Lipids 23(6): 534–538.
Buhr, RJ, JK Northcutt, CE Lyon and GN Rowland, 1998. Influence of time off feed on broiler Viscera weight, diameter and shear. Poultry Science 77(5): 758–761, abstract.
Byrd, JA, DE Corrier, ME Hume, RH Bailey, LH Stanker and BM Hargis, 1998. Effect of feed withdrawal on campylobacter in the crops of market age broiler chickens. Avian Diseases 42(4): 802–806,. abstract.
Chaumont JP and D Leger, 1992. Campaign against allergic moulds in dwellings. Inhibitor properties of essential oil geranium "Bourbon", citronellol, geraniol and citral. Ann Pharm Er 50(3): 156–166., abstract.
Crowell, PL and MN Gould, 1994. Chemoprevention and therapy of cancer by d–limonene. Crit Rev Oncog 5(1): 1–22.
Crowell, PL, S Ayoubi and YD Burke, 1996. Antitumorigenic effects of limonene and perillyl alcohol against pancreatic and breast cancer. Adv Exp Med Biol 401: 131–136.
Elegbede, JA, CE Elson, A Qureshi, MA Tanner and MN Gould, 1984. Inhibition of DMBA–induced mammary cancer by monoterpene d–limonene. Carcinogenesis 5(5): 661–664.

Elegbede, JA, CE Elson, A Qureshi, MA Tanner and MN Gould, 1986. Regression of rat primary mammary tumors following dietary d–limonene. J Natl Cancer Inst 76(2): 323–325.
Elson, CE and SG Yu, 1994. The chemoprevention of cancer by mevalonate–derived constituents of fruits and vegetables. J Nutr. 124: 607–614., abstract.
Hooser, SB, VR Beasly and JJ Everitt, 1986. Effects of an insecticidal dip containing d–limonene in the cat. J Am Vet Med Assoc 189(8): 905–908.
Ishii, E., 1993. Antibacterial activity of teprenone, a non water–soluble antiulcer agent, against Helicobacter pylori. Int J Med Microbiol Virol Parasitol Infect Dis 280(1–2): 239–243.
Karlson, J, AK Borg, R Unelius, MC Shoshan, N Wilking, U Ringborg and S Linder, 1996. Inhibition of tumor cell growth by monoterpenes in vitro: evidence of a Ras–independent mechanism of action. Anticancer Drugs 7(4): 422–429.
Kim J, M Marshall and C Wei, 1995. Antibacterial activity of some essential oil components against five foodborne pathogens. J Agric Food Chem 43: 2839–2845.
Mikhlin Ed, VP Radina, AA Dmitrossky. LP Blinkova and LG Button, 1983. Antifungal and antimicrobic activity of some derivatives of beta–ionone and vitamin A. Prikl Biokhim Mikrobiol. 19: 795–803, abstract.
Moleyar V and P Narasimham, 1992. Antibacterial activity of essential oil components. Int J Food Microbiol 16(4): 337–342., abstract.
Onawunmi, GO, 1989. Evaluation of the antimicrobial activity of citral. Letters in Applied Microbiology 9(3): 105–108.
Pattnaik, S, VR Subramanyan, M Bapaji and CR Kole, 1997. Antibacterial and antifungal activity of aromatic constituents of essential oils. Microbios 89(358): 39–46.
Salt, SD, S Tuzun and J Kuc, 1986. Effects of B–ionone and abscisic acid on the growth of tobacco and resistance to blue mold. Mimicry the effects of stem infection by Peronospora tabacina. Adam Physiol Molec Plant Path 28: 287–297, abstract.
Yu, SG, PJ Anderson and CE Elson, 1995. The efficacy of B–ionone in the chemoprevention of rat mammary carcinogenesis. J Agric Food Chem 43: 2144–2147., abstract.

* cited by examiner

Primary Examiner—Rebecca Cook

(57) ABSTRACT

A method to reduce the gastro-intestinal bacterial load by feeding a diet or a solution containing a terpene, terpene mixture or a liposome-terpene combination 1 to 25 days before slaughter.

8 Claims, No Drawings

REDUCTION OF GASTRO-INTESTINAL BACTERIAL LOAD

BACKGROUND OF THE INVENTION

1. Field of the Invention

A method to decrease the gastro-intestinal bacterial load of animals by feeding a diet or solution containing terpenes and/or liposome-terpene combination 1 to 25 days before slaughter.

2. Discussion of the Background

In a normal, steady-state eating pattern, the intestine of animals is usually empty 4 to 6 hours after a feeding. For this reason, feed is withdrawn 4 to 12 hours before slaughter. This procedure is not without compromises. Because of the lack of feed, the animal loses weight and the intestinal wall becomes fragile and prone to rupture. This results in spilling of the intestinal content during slaughter and evisceration (Buhr et al, 1998). In the case of poultry, spilling causes contamination with whatever bacteria is present. Another problem with feed withdrawal is the increased number of animals that will practice coprophagy (eating of feces), resulting in higher bacterial counts in the intestinal contents and the final processed products (meat) (Byrd et al, 1998). When the feed is not withdrawn, the crop and intestinal tract are full of feed, which also results in breaking and spilling of the contents. Contamination can also originate from bacteria present in feathers and skin. Feed withdrawal may reduce the contamination of carcasses but it also results in a decline of volatile fatty acids and a resultant increase in cecal pH which is correlated with an increase in fecal shedding of foodborne pathogens.

There are not any safe procedures or products that can decrease carcass contamination or decrease the loss in animal weight. There are chemicals that recently have shown promising results. The positive results from the use of terpenes have been reported.

Terpenes (pinene, nerol, citral, menthol, d-limonene and others) are widespread in nature, mainly in plants as constituents of essential oils. Their building block is the hydrocarbon isoprene $(C_5H_8)_n$. Terpenes are effective, nontoxic dietary antitumor agents which act through a variety of mechanisms of action and hold promise as a novel class of antitumor drugs for human cancer (Crowell and Gould, 1994 and Crowell et al, 1996). Geraniol, tocotrienol, perillyl alcohol, b-ionone and d-limonene suppress hepatic HMG-COA reductase activity, a rate limiting step in cholesterol synthesis, and modestly lower cholesterol levels in animals (Elson and Yu, 1994). D-limonene and geraniol reduced mammary tumors (Elegbede et al, 1984 and 1986 and Karlson et al, 1996) or suppressed the growth of transplanted tumors(Yu et al, 1995).

Terpenes (citral, geraniol, eugenol, menthol, cinnamic aldehyde) have also been found to inhibit the in-vitro growth of bacteria and fungi (Chaumont and Leger, 1992, Moleyar and Narasimham, 1992 and Pattnaik, et al 1997) and some internal and external parasites (Hooser, et al, 1986). Geraniol was found to inhibit growth of candida albicans and saccharomyces cerevisiae strains by enhancing the rate of potassium leakage disrupting membrane fluidity (Bard, et al, 1988). B-ionone has antifungal activity which was determined by inhibition of spore germination, and growth inhibition in agar (Mikhlin et al, 1983 and Salt et al, 1986). Teprenone has an antibacterial effect on H. pylori (Ishii, 1993). Solutions of 11 different terpenes were effective in inhibiting the growth of pathogenic bacteria in in-vitro tests; levels ranging between 100 ppm and 1000 ppm were effective. The terpenes were diluted in water with 1% tween 20 (Kim et al, 1995).

There may be different modes of action of terpenes against bacteria. They could (1)interfere with the phospholipid bilayer of the cell membrane (2)impair a variety of enzyme systems (HMG-reductase) and (3) destroy or inactivate genetic material.

The addition of terpenes to the diet or to the drinking water would reduce the bacterial load, not only in feed and water, but also in the intestine. Pathogenic bacteria like salmonella, E. coli and listeria would be decreased, thereby reducing the chance of contamination and the risk of pathogenic microorganisms in the final edible product.

SUMMARY OF THE INVENTION

A method for the reduction of the gastrointestinal bacterial load by feeding a diet or solution containing a terpene, a terpene mixture or a liposome-terpene combination.

DESCRIPTION OF THE PREFERRED EMBODIMENTS

Terpenes, which are GRAS (Generally Recognized As Safe) have been found to inhibit the growth of cancerous cells, decrease tumor size, decrease cholesterol level and have a biocidal effect on microorganisms in vitro. Onawunmi (1989) showed that media with more than 0.01% citral reduced the concentration of E. coli and at 0.08% there was a bactericidal effect. Barranx, et al(1998) teach us a terpene formulation, based on pine oil, used as disinfectant or antiseptic cleaner. Koga, et al (1998) teach that a terpene found in rice has antifungal activity. Neither of them suggested the use of a terpene or terpene mixture for the internal disinfection of the gastrointestinal tract of animals by the addition of a terpene, a terpene mixture or a liposome-terpene combination into feed or water.

Several U.S. Patents (U.S. Pat. No. 5,547,677, U.S. Pat. No. 5,549,901, U.S. Pat. No. 5,618,840, U.S. Pat. No. 5,629,021, U.S. Pat. No. 5,662,957, U.S. Pat. No. 5,700,679, U.S. Pat. No. 5,730,989)teach us that certain types of oil-in-water emulsions have antimicrobial, adjuvant and delivery properties. By encapsulating terpenes within these emulsions or mixing them together, the antimicrobial effect will be increased, i.e. (1) the liposome will disrupt the bacterial membrane and (2) the terpenes will be more effective in disrupting cytoplasmatic enzymes.

Some procedures are used in order to change the microflora of animals, but they will not alter bacteria number. Competitive Exclusion (CE) has been utilized to decrease the incidence of pathogenic organism in animals. CE will create a competition for nutrients between good bacteria and pathogenic bacteria, but it is unlikely that the usage of beneficial bacteria can significantly reduce the bacteria count in the final processed product. The animal industry feeds low levels of antibiotics to decrease bacterial exposure, which results in an improvement in health and performance, but does not eliminate great numbers of bacteria. Currently federal agencies have approved the use of low level radiation to kill bacteria in meat, but the use of radiation at any level will always be challenged by concerned groups.

The short use or continuous use of a terpene mixture or liposome-terpene composition will have the same effect as antibiotic feeding, with the advantage that terpenes will not result in resistant bacteria or drug residues in animal produce. Short term or continuous terpene feeding can be obtained by adding the terpene, terpene mixture or liposome-terpene composition in the feed or in the drinking water of animals. The terpenes can also be delivered encapsulated within liposomes.

It will be apparent for those skilled in the art that the aforementioned objects and other advantages may be further achieved by the practice of the present invention.

1.—Preparation of the Terpene Mixture

The terpene or terpene mixture consists of a blend of GRAS terpenes with a GRAS surfactant or surfactant combination. The ratio of terpene or terpene mixture is from 50 to 99% and surfactant ratio from 1 to 50% of the mixture. The terpene or terpene mixture is comprised of natural or synthetic terpenes. The preferred terpenes are citral, b-ionone, eugenol, geraniol, terpeniol, carvacrol, anethole and other terpenes with similar qualities. The surfactant is preferably polysorbate-80 or other suitable GRAS surfactant or surfactant combination.

2.—In-vitro Effectiveness of Terpenes Against E. Coli

This example demonstrates the effect of terpenes on the cell membrane fragility of E. coli, which is considered indicative of other pathogenic bacteria such as salmonella and listeria. Lysis of the cell membrane was monitored by the determination of galactosidase activity. B-galactosidase is a well characterized cytosolic enzyme in bacteria. This enzyme is inducible in the presence of isopropyl-1-thiogalactosidase (IPTG) and assayed colorimetricaly with substrate o-nitro-phenyl-B-D-galactoside (ONPG). ONPG is cleaved to release o-nitrophenol with peak absorvance at 420 nm. Since intact E. coli is impermeable to both ONPG and the enzyme, the cells have to be lysed prior to enzymatic assay. Therefore the ability of terpenes to lyse E. coli can be measured with this enzymatic assay and compared to known lysing agents. The procedure used was as follows: E. coli strains AW574 or AW405 were cultured overnight in 10 ml tryptone broth with 1 nM IPTG at 35° C. Cells were allowed to growth after an absorbance equal to 0.9 was reached. Cells were harvested, washed with phosphate buffer and resuspended to an absorbance equal to 0.5. One tenth of a ml of the bacteria culture was added to 0.9 ml of buffer, warmed to 30° C. and then 80 ul of terpenes (85% terpenes and 15% polysorbate-80), 80 ul water (background) or 40 ul chloroform plus 40 ul 1% SDS in water (positive control) were added. After the addition of the lysing agents the tubes were mixed for 10 seconds and 0.2 ml of ONPG (4 mg/ml water) was added, then incubated for 5 minutes. The enzyme activity was stopped with 0.5 ml of 1 M sodium carbonate. After being centrifuged for 3 minutes at 1,500×g, supernatant was transferred to cuvettes and read at 420 nm. The relative degree of lysis caused by terpenes was calculated as follows:

$$100\times(OD\ terpenes-OD\ water)/(OD\ chloroform-OD\ water)$$

TABLE 1

Lysis of E. coli by Terpenes

| | Terpenes (uM) | Relative lysis % |
|---|---|---|
| Carvone | 404,000 | NM* |
| | 40,400 | 54 |
| | 4,040 | 22 |

TABLE 1-continued

Lysis of E. coli by Terpenes

| | Terpenes (uM) | Relative lysis % |
|---|---|---|
| | 404 | 3.2 |
| Geraniol | 363,000 | NM |
| | 36,300 | 96 |
| | 3,630 | 98 |
| | 363 | 34 |
| | 36.3 | 4 |
| | 3.63 | 2.4 |
| b-Ionone | 308,000 | NM |
| | 30,800 | NM |
| | 3,080 | NM |
| | 308 | 52 |
| | 30.8 | 44 |
| | 3.08 | 23 |
| | 0.308 | 4.78 |
| | 0.0308 | 1.3 |
| 80 ul Polysorbate-80 | | 3.2 |
| 80 ul Polysorbate-80 + SDS + Chloroform | | 100 |
| SDS + Chloroform | | 100* |

*Lysis due to chloroform and SDS combination was considered to be 100%.
*NM, not measurable due to formation of turbid colloidal solution.

3.—Dosification in Animal Feed

The terpene or terpene mixture is sprayed onto the complete feed during or after mixing or after pelletizing or storage. The rate to use varies from 5 to 10,000 ppm.

4.—Dosification in Water Supply

The terpene or terpene mixture is added to the drinking water supply at a rate of 5 to 10,000 ppm.

5.—Feeding Program

Commercially, feed is withdrawn 4 to 8 hours before slaughter. In order to decrease bacterial load before slaughter, the next procedure is to be followed:
1) Feed is withdrawn 12 hours before slaughter.
2) Animals are fasted for 4 hours.
3) Diet with terpenes is fed 8 hours before slaughter.
4) Feed animals for 2 to 4 hours.
5) Withdraw feed 4 to 6 hours before slaughter.

An alternative method is to continuously feed the terpene or the terpenes mixture from 1–25 days before slaughter.

6.—Watering Program

Terpene or terpene mixture is added to the drinking water and given continuously 1–25 days before slaughter.

7.—Synergistic Effect of Liposome-terpene Combination

The antimicrobial benefit of terpenes has been previously demonstrated. Certain types of liposomes, depending on the charge they possess, can be effective against gram-positive or gram-negative bacteria. This liposome-terpene combination will produce a synergistic effect: (1) the liposome will disrupt the bacterial membrane and (2) the terpenes will be more effective in disrupting cytoplasmatic enzymes, thereby producing a more efficient antimicrobial effect.

It will be apparent for those skilled in the art that a number of modifications and variations may be made without departing from the scope of the present invention as set forth in the appending claims.

References

1. Bard, M, M R Albert, N Gupta, C J Guuynn and W Stillwell, 1988. Geraniol interferes with membrane functions in strains of Candida and Saccharomyces. Lipids 23(6): 534–538.
2. Buhr, R J, J K Northcutt, C E Lyon and G N Rowland, 1998. Influence of time off feed on broiler viscera weight, diameter and shear. Poultry Science 77(5): 758–764.
3. Byrd, J A, D E Corrier, M E Hume, R H Bailey, L H Stanker and B M Hargis, 1998. Effect of feed withdrawal on campylobacter in the crops of market age broiler chickens. Avian Diseases 42(4): 802–806.
4. Barranx A, M Barsacq, G Dufau and J P Lauilhe, 1998. Disinfectant or antiseptic composition comprising at least one terpene alcohol and at least one bactericidal acidic surfactant, and use of such a mixture. U.S. Pat. No. 5,763,468.
5. Chaumont J P and D Leger, 1992. Campaign against allergic moulds in dwellings. Inhibitor properties of essential oil geranium "Bourbon", citronellol, geraniol and citral. Ann Pharm Fr 50(3): 156–166.
6. Crowell, P L and M N Gould, 1994. Chemoprevention and therapy of cancer by d-limonene. Crit Rev Oncog 5(1): 1–22.
7. Crowell, P L, S Ayoubi and Y D Burke, 1996. Antitumorigenic effects of limonene and perillyl alcohol against pancreatic and breast cancer. Adv Exp Med Biol 401: 131–136.
8. Elegbede, J A, C E Elson, A Qureshi, M A Tanner and M N Gould, 1984. Inhibition of DMBA-induced mammary cancer by monoterpene d-limonene. Carcinogenesis 5(5): 661–664.
9. Elegbede, J A, C E Elson, A Qureshi, M A Tanner and M N Gould, 1986. Regression of rat primary mammary tumors following dietary d-limonene. J Natl Cancer Inst 76(2): 323–325.
10. Elson, C E and S G Yu, 1994. The chemoprevention of cancer by mevalonate-derived constituents of fruits and vegetables. J Nutr. 124: 607–614.
11. Hooser, S B, V R Beasly and J J Everitt, 1986. Effects of an insecticidal dip containing d-limonene in the cat. J Am Vet Med Assoc 189(8): 905–908.
12. Ishii, E.,1993. Antibacterial activity of teprenone, a non water-soluble antiulcer agent, against Helicobacter pylori. Int J Med Microbiol Virol Parasitol Infect Dis 280(1–2): 239–243.
13. Karlson, J, A K Borg, R Unelius, M C Shoshan, N Wilking, U Ringborg and S Linder, 1996. Inhibition of tumor cell growth by monoterpenes in vitro: evidence of a Ras-independent mechanism of action. Anticancer Drugs 7(4): 422–429.
14. Kim J, M Marshall and C Wei, 1995. Antibacterial activity of some essential oil components against five foodborne pathogens. J Agric Food Chem 43: 2839–2845.
15. Koga, J, T Yamauchi, M Shimura, Y Ogasawara, N Ogasawara and J Suzuki, 1998. Antifungal terpene compounds and process for producing the same. U.S. Pat. No. 5,849,956.
16. Mikhlin E D, V P Radina, A A Dmitrossky. L P Blinkova and L G Button, 1983. Antifungal and antimicrobic activity of some derivatives of beta-ionone and vitamin A. Prikl Biokhim Mikrobiol. 19: 795–803.
17. Moleyar V and P Narasimham, 1992. Antibacterial activity of essential oil components. Int J Food Microbiol 16(4): 337–342.
18. Onawunmi, G O, 1989. Evaluation of the antimicrobial activity of citral. Letters in Applied Microbiology 9(3): 105–108.
19. Pattnaik, S, V R Subramanyan, M Bapaji and C R Kole, 1997. Antibacterial and antifungal activity of aromatic constituents of essential oils. Microbios 89(358): 39–46.
20. Salt, S D, S Tuzun and J Kuc, 1986. Effects of B-ionone and abscisic acid on the growth of tobacco and resistance to blue mold. Mimicry the effects of stem infection by Peronospora tabacina. Adam Physiol Molec Plant Path 28: 287–297.
21. Wright, D C, 1996. Antimicrobial oil-in-water emulsions. U.S. Pat. No. 5,547,677.
22. Wright, D C, 1996. Antimicrobial oil-in-water emulsions. U.S. Pat. No. 5,549,901.
23. Wright, D C, 1997. Antimicrobial oil-in-water emulsions. U.S. Pat. No. 5,618,840.
24. Wright, D C, 1997. Micellar nanoparticles. U.S. Pat. No. 5,629,021.
25. Wright, D C, 1997. Oil containing lipid vesicles with marine applications. U.S. Pat. No. 45,662,957.
26. Wright, D C, 1997. Lipid vesicles having a bilayer containing a surfactant with anti-viral and spermicidal activity. U.S. Pat. No. 5,700,679.
27. Wright, D C, 1998. Oral vaccine against gram negative bacterial infection. U.S. Pat. No. 5,730,989.
28. Yu, S G, P J Anderson and C E Elson, 1995. The efficacy of B-ionone in the chemoprevention of rat mammary carcinogenesis. J Agri Food Chem 43: 2144–2147.

What we claim is:

1. A method for inhibiting the growth of pathogenic microorganisms in the gastro-intestinal tract of animals relative to control animals by orally feeding to said animals a composition comprising a terpene, a mixture of terpenes or a liposome-terpene(s) combination and a surfactant 1 to 25 days before slaughtering said animals for human consumption; said terpenes selected from the group consisting of b-ionone, carvone and geraniol.

2. The method of claim 1, wherein the terpene or terpene mixture consists of 50 to 99% terpenes and 1 to 50% surfactant.

3. The method of claim 1, wherein the liposome-terpene(s) combination comprises the encapsulation of a terpene or terpene mixture.

4. The method of claim 1, wherein the liposome-terpene(s) combination comprises mixing liposomes with a terpene or terpene mixture.

5. The method of claim 1, wherein the terpene or terpene mixture are natural or synthetic terpenes selected from citral, b-ionone, geraniol, carvacrol, eugenol, carvone, terpeniol and anethole; and the surfactant is selected from polysorbate-80, polysorbate-20, polysorbate-40, polysorbate-60, polyglyceryl esters, polyglyceryl monooleate, decaglyceryl monocaprylate, propylene glycol dicaprilate and triglycerol monostearate or a combination thereof.

6. The method of claim 1, wherein the terpene, the mixture of terpenes or the liposome-terpene(s) combination is added to the animal diet at a rate of 5–10,000 ppm (mg/kilogram feed) and fed 1 to 25 days before slaughtering animals for human consumption.

7. The method of claim 1, wherein the terpene, the mixture of terpenes or the liposome-terpene(s) combination is added to the drinking water at a rate of 5–10,000 ppm (mg/liter of water) and given 1 to 25 days before slaughtering animals for human consumption.

8. The method of claim 1, wherein said animals are selected from avian, bovine, porcine, equine, ovine, caprine and rodents.

* * * * *